(12) United States Patent
Bachmann

(10) Patent No.: US 8,753,355 B2
(45) Date of Patent: *Jun. 17, 2014

(54) UMBILICAL CORD TAB

(76) Inventor: Jaycinth Elona Bachmann, Port St. Lucie, FL (US)

( * ) Notice: Subject to any disclaimer, the term of this patent is extended or adjusted under 35 U.S.C. 154(b) by 105 days.

This patent is subject to a terminal disclaimer.

(21) Appl. No.: 13/444,812

(22) Filed: Apr. 11, 2012

(65) Prior Publication Data

US 2012/0192873 A1    Aug. 2, 2012

Related U.S. Application Data

(63) Continuation-in-part of application No. 12/214,307, filed on Jun. 18, 2008.

(60) Provisional application No. 60/934,967, filed on Jun. 18, 2007.

(51) Int. Cl.
*A61B 17/50* (2006.01)

(52) U.S. Cl.
USPC .......................................... 606/131; 606/119

(58) Field of Classification Search
USPC ......... 606/116, 117, 120, 125, 131, 151, 157; 604/289, 303, 385.01; 128/846; 602/41, 42, 60, 61, 72, 78, 79
See application file for complete search history.

(56) References Cited

U.S. PATENT DOCUMENTS

| | | |
|---|---|---|
| 3,016,056 A | 1/1962 | Jacobs |
| 3,674,032 A | 7/1972 | Minganti |
| 5,009,657 A | 4/1991 | Cotey |
| 5,667,516 A | 9/1997 | Allen |
| 5,817,103 A | 10/1998 | Bell |
| 5,836,930 A | 11/1998 | Lantz et al. |
| 6,318,371 B1 | 11/2001 | Tyszkiewicz |
| 6,875,200 B1 | 4/2005 | Ajagbe |
| 7,402,164 B2 | 7/2008 | Watson, Jr. et al. |
| 7,770,237 B1 | 8/2010 | Wright |
| 7,882,570 B2 | 2/2011 | Krier |
| 2002/0198535 A1 | 12/2002 | Watson, Jr. et al. |
| 2003/0036733 A1 | 2/2003 | Martin |
| 2003/0195476 A1 | 10/2003 | Martin |
| 2004/0172043 A1 | 9/2004 | Watson, Jr. et al. |
| 2005/0090836 A1* | 4/2005 | Stracener ...................... 606/119 |
| 2008/0077067 A1 | 3/2008 | Mata |
| 2008/0287960 A1 | 11/2008 | Watson, Jr. et al. |
| 2009/0292295 A1 | 11/2009 | Peñuñuri |
| 2010/0137877 A1 | 6/2010 | Rice et al. |

* cited by examiner

*Primary Examiner* — Ryan Severson
*Assistant Examiner* — Katherine M Shi
(74) *Attorney, Agent, or Firm* — Scully, Scott, Murphy & Presser, P.C.

(57) ABSTRACT

The present invention relates to a device and method for cleaning an infant's navel and umbilical cord stump. In particular, the present invention provides a device that eliminates the need for a user to physically hold the umbilical cord stump and allows trapped dirt and moisture to be accessed and removed easily, avoiding premature detachment of the umbilical cord stump and minimizing the risk of infection. The device of the present invention also protects the skin surrounding an infant's navel from cleaning solutions while the infant' navel and umbilical cord stump is being cleaned.

14 Claims, 5 Drawing Sheets

UMBILICAL CORD TAB

This application is a Continuation in Part Application of application Ser. No. 12/214,307, filed Jun. 18, 2008, which in turn claims priority to Provisional Patent Application Ser. No. 60/934,967, filed Jun. 18, 2007.

FIELD OF THE INVENTION

The present invention relates to a device and method for cleaning an infant's navel and umbilical cord stump. In particular, the present invention provides a device that eliminates the need for a user to physically hold the umbilical cord stump and allows trapped dirt and moisture to be accessed and removed easily, avoiding premature detachment of the umbilical cord stump and minimizing the risk of infection. The device of the present invention also protects the skin surrounding an infant's navel from cleaning solutions while the infant's navel and umbilical cord stump are being cleaned.

BACKGROUND

During pregnancy, the developing fetus receives nutrients and oxygen through the placenta, which is connected to the inner wall of the mother's uterus. The placenta is connected to the fetus by the umbilical cord through an opening in the fetus' abdomen. After birth, the umbilical cord is clamped and cut close to the body, leaving an umbilical stump, which falls off naturally, typically in about 10-21 days.

While the umbilical cord stump remains attached to the newborn infant, the stump and the infant's navel must be kept clean and dry, due to the risk of bacterial infection of the umbilical cord stump. Umbilical cord stump care typically involves cleaning the area surrounding the umbilical cord stump with cleaning solutions, including, for example, hydrogen peroxide solution, isopropyl alcohol, anti microbial solutions, anti bacterial solutions and the like. Adequate cleaning requires cleaning the base of the umbilical cord stump, which is often tucked under folds of skin and therefore difficult to reach.

There are existing devices that can be used in the care and management of the umbilical cord following birth.

For example, U.S. Pat. No. 7,882,570B2 discloses an infant garment [that] preserves body heat and facilitates access to a localized region of the body surface of a patient. The garment has a slit on the front that allows the region of the patient's body surface to be monitored and, if necessary, treated without requiring removal of the garment. The garment also has sleeves with cuffs that can be reversibly folded to cover or uncover the hand-openings in the distal ends of the sleeves.

In another example, U.S. Pat. No. 7,770,237B2 discloses a baby garment for accessing and protecting the umbilical cord for allowing the cleaning of and protecting a baby's umbilical cord. The baby garment for accessing and protecting the umbilical cord includes a piece of material having front and back portions and also having an umbilical-exposing hole being disposed through the front portion and about the baby's umbilical cord to allow a user to effectively clean the umbilical cord without the user having to remove the baby garment from the baby, and an oversized cover being hingedly attached to the front portion and being fastenably closeable and loosely disposed over the umbilical cord to effectively protect and not to irritate the umbilical cord.

In another example, U.S. Pat. No. 7,402,164B2 discloses a novel umbilical cord clamp and a combined umbilical cord clamp and cutter . . . for clamping and cutting umbilical cords in one motion. The cutter comprises two shells joined by a longitudinal hinge. A transverse blade is mounted in one shell, and a cutting support is mounted in the other shell across from the blade. One or more removable clamps may be engaged with the shells to be removable from the shells after cutting. Alternatively, a self-winding or plastically deformable band may be engageable with the shells. The cutter and its associated removable clamp(s) may be coordinated with an identifier, such as a color, number, or letter. Blood sampling and diagnostic features may be included with the cutter. The removable clamps may have an openable closure.

In another example, U.S. Pat. No. 6,875,200B1 discloses a bandage for protecting the skin of an infant's stomach surrounding an umbilical cord stump from the irritating effects of medicinal solutions. The bandage is substantially flat and has an absorbent upper surface, a substantially nonabsorbent lower surface, and a circular central cutout wherefrom the umbilical cord stump may be extended. The bandage has a flap closure portion comprising a bottom flap and an overlapping top flap. The top flap has adhesive on its lower surface whereby the top flap maybe attached to the bottom flap. In use, the bandage is placed on the infant's stomach with the umbilical cord stump extending therefrom. Then, the lower surface of the top flap is attached to the underlying bottom flap. With the protective bandage in place, a variety of solutions may be applied to the umbilical cord stump without irritating the sensitive skin of the infant's stomach.

In another example, U.S. Pat. No. 5,836,930A discloses [an] absorbent article [that] comprises a substantially liquid-impermeable outer cover member having a length and a width. The outer cover provides a rear waistband portion and a front waistband portion, and has a layer of polymer film material on an outer surface of the front waistband portion of the outer cover. A liquid permeable topsheet layer is provided for contacting a wearer's skin, and an absorbent body is interposed between the outer cover and the topsheet layer. The absorbent body has a length and width which are smaller than the outer cover length and width, thereby providing end margins and side margins of the outer cover. An adhesive fastening mechanism adheres to the film layer to secure the front and rear waistband portions of the outer cover about the wearer. An elastic member is connected to provide elasticized gathers along a cross-direction of the rear waistband portion of the outer cover. An outermost layer of substantially non-wettable, resilient material is connected to overlie the polymer film of the outer cover along the front waistband portion of the outer cover, thereby sandwiching the polymer film between the top sheet layer and the outermost layer of resilient material. The outermost resilient material has a lengthwise extent, which is less than the length of the outer cover.

In another example, U.S. Pat. No. 5,817,103A discloses an obstetrical combined disinfectant, clamp, cutter and containment system for umbilical cords, being housed in a comprehensive unit and having increased efficiency in the area of motion saving and exposure to infectious organisms during the birthing process and when exposure to infectious organisms is undesirable. A housing contains three umbilical clamps as part of the overall housing of the unit and two pair of serrated, cutting blades incorporated into the housing by way of bonding to the housing structure of the unit. After the baby's umbilical cord is placed horizontally in the unit, the disinfectant makes contact with the cutting sites of the umbilical cord, followed by the closing of the unit, simultaneously clamping and cutting the cord, whereafter the unit is twisted at the perforated midpoint, separating the fetal umbilical stump from the maternal end of the umbilical cord. Following separation, both maternal and infant cord ends remain in a clean environment, being totally enclosed in individual compartments. The maternal portion of the device is easily discarded after expulsion of the placenta. The infant's unit will remain in place from five to seven (5-7) days, at which point the cord gradually atrophies and the unit falls off.

In another example, U.S. Pat. No. 5,009,657 discloses an umbilical cord cutting and clamping device is used with a fetal cord end clip to permit a physician to quickly sever an umbilical cord and securely clamp the fetal cord end.

In another example, U.S. patent application US20100137877A1 discloses a combined umbilical cord clamp, cutter, disinfectant, and data collecting system which reduces the risk of cord infections due to unsanitary birth conditions.

In another example, U.S. patent application US20090292295A1 discloses an umbilical cord ligature device comprising a flexible latex ligature that is pre-assembled on a semi-rigid plastic ring. The umbilical cord is slipped through the device to a point close to the baby's abdominal wall, and with a twist of fingers, the latex ligature is then released from the ring over the umbilical cord, where it stays compressing the cord until it dehydrates and falls off. The pressure that the ligature exerts around the umbilical cord during its dehydration period makes hemorrhages virtually impossible.

In another example, U.S. patent application US20080287960A1 discloses an umbilical cord clamping and cutting device assembled within opposing shields for minimizing the spray of blood during severing of the umbilical cord.

In another example, U.S. patent application US20080077067A1 discloses a hygienic applicator for applying a cleaning solution to the umbilical cord area of a newborn. The hygienic applicator includes a support member that is substantially cylindrical in shape. The support member includes two ends. Superposed on each end is a tip made from an absorbent material that is designed to retain a desired cleaning solution and assist the user in applying the cleaning solution to the desired area. The support member is further enclosed in a container having a cavity of sufficient size to substantially enclose the support member therein and prevent the evaporation of the cleaning solution for the applicator. The container further includes an opening mechanism for facilitating the easy opening of the container.

In another example, U.S. patent application US20050090836A1 discloses a care kit for an umbilical cord for a newborn child. The care kit comprises a supply of materials necessary to care for an umbilical cord until it falls off which is estimated to be about two weeks. The present invention includes a wet umbilical cord cleaner, which have been wet with a disinfectant, and a dry umbilical cord cleaner to clean off any excess alcohol. Also included are clear adhesive dressings which are used during sponge baths to keep the umbilical cord dry. Additionally provided, are a convenient carrying case along with instructions for the umbilical cord care to prepare the parent for reporting back to the baby's doctor.

In another example, U.S. patent application US20040172043A1 discloses a novel umbilical cord clamp and a combined umbilical cord clamp and cutter are provided for clamping and cutting umbilical cords in one motion. The cutter comprises two shells joined by a longitudinal hinge. A transverse blade is mounted in one shell, and a cutting support is mounted in the other shell across from the blade. One or more removable clamps may be engaged with the shells to be removable from the shells after cutting. Alternatively, a self-winding or plastically deformable band may be engageable with the shells. The cutter and its associated removable clamp(s) may be coordinated with an identifier, such as a color, number, or letter. Blood sampling and diagnostic features may be included with the cutter. The removable clamps may have an openable closure.

In another example, U.S. patent application US20030195476A1 discloses an apparatus useful for umbilical cord care and method of its use are disclosed. The apparatus provides an injector that is detachably connected to a disposable applicator. The umbilical cord care apparatus may be provided as a kit, particularly suited for use at home.

In another example, U.S. patent application US20030036733A1 discloses an apparatus useful for umbilical cord care and method of its use are disclosed. The apparatus provides an injector that is detachably connected to a disposable applicator. The umbilical cord care apparatus may be provided as a kit, particularly suited for use at home.

In another example, U.S. patent application US20020198535A1 discloses an umbilical cord clamp and a combined umbilical cord clamp and cutter . . . for clamping and cutting umbilical cords in one motion. The cutter comprises two shells joined by a longitudinal hinge.

In spite of the importance of proper umbilical cord stump care, the current methods and devices, including those devices disclosed above, have several disadvantages, including the inability to gain access to and sufficiently clean the area around the base of the umbilical cord stump. Furthermore, the person cleaning the umbilical cord stump frequently has to hold the umbilical cord stump, moving and tugging on the stump, thereby increasing the risk of detaching the umbilical cord stump prematurely. Additionally, existing devices do not protect the infant's skin from the chemicals used to clean the umbilical cord stump.

Therefore, there exist a need for a device that protects the infant's skin from the chemicals used to clean the umbilical cord stump, that provides protection and support for the umbilical cord stump during cleaning, that enhances the full cleaning of the umbilical cord stump and surrounding area, and that reduces the risk that the umbilical cord stump detaches prematurely.

SUMMARY

In one embodiment, the present invention provides a device that protects the skin surrounding an infant's navel from cleaning solutions, aids in manipulating the infant's umbilical cord stump, and provides support and protection to the infant's umbilical cord stump while a user cleans the infant's navel and umbilical cord stump, comprising:

a. an upper portion and a lower portion, the upper portion consisting of a wall extending upward from a junction of the lower portion and a base of the wall, the upper portion defining by partially encircling a first area of the lower portion, the first area having a central orifice with a second area less than the first area, wherein the partial encirclement of the first area by the wall provides an opening; and b. a third area of the lower portion, consisting of two flanges extending laterally outward from the first area at the junction of the base of the wall of the upper portion and the first area of the lower portion, each flange having a fourth area.

In one embodiment, the present invention provides a method for cleaning an infant's umbilical cord stump without having to physically touch the umbilical cord, comprising the steps of:

a. placing the device of the present invention on the infant's abdomen, such that the upper portion faces away from the infant, the umbilical cord stump is inserted through the central orifice;
b. contacting the underside of the lower portion with the skin surrounding the infant's navel;
c. moving the device of the present invention to contact the umbilical cord stump with the perimeter of the central orifice;
d. displacing the umbilical cord stump, exposing an area to be cleaned; and
e. cleaning the exposed area.

In one embodiment, the present invention provides a kit, comprising a device of the present invention, cleaning solutions and instructions on how to use the device of the present invention to clean an infant's umbilical cord stump without having to physically touch the umbilical cord stump.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person of ordinary skill in the art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
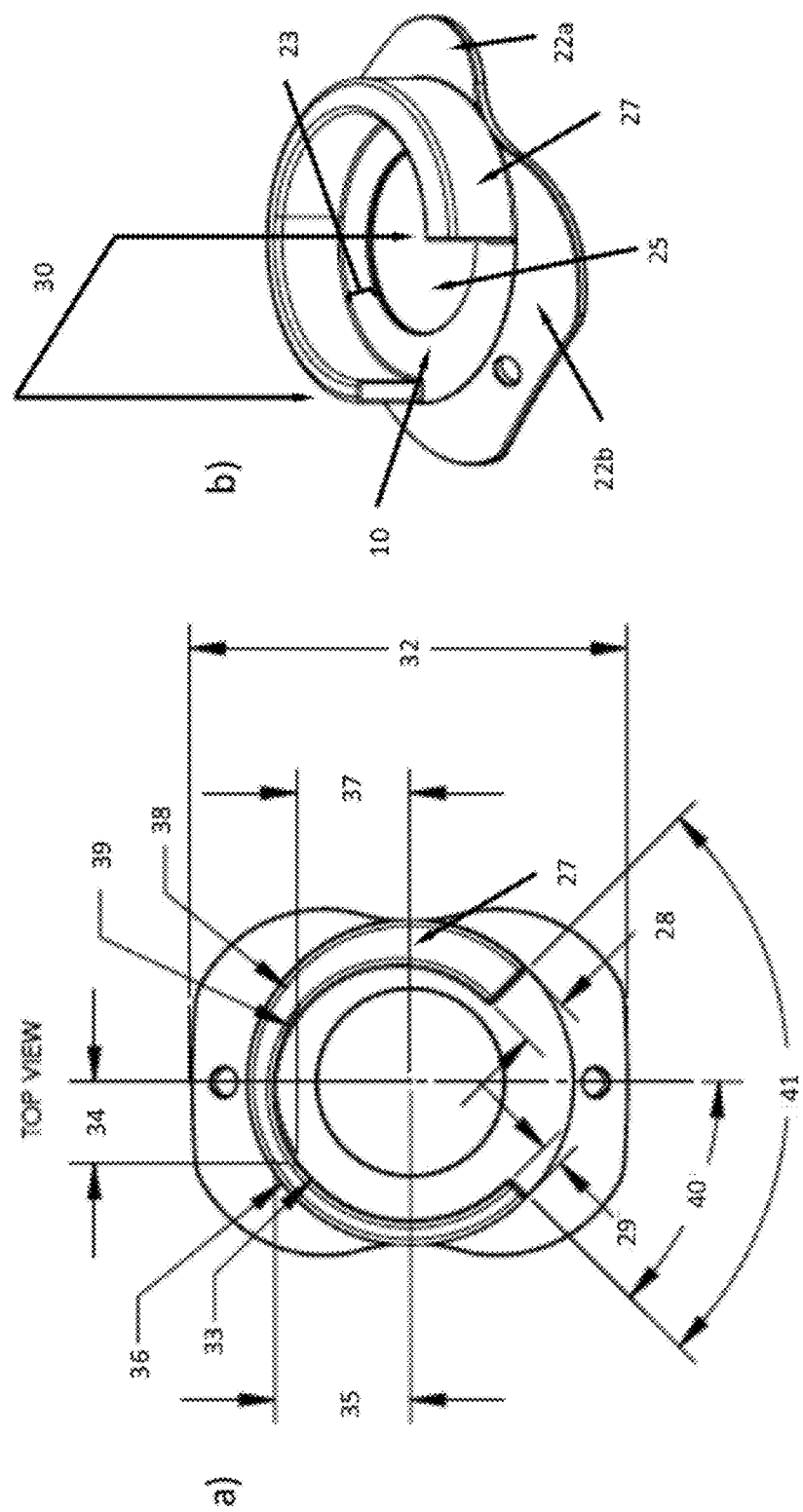
FIG. 1, panel a) depicts a plan view of one embodiment of the device of the present invention, looking from the top, showing the upper portion comprising a wall (27) having a variable thickness, with a minimum thickness (29) and a maximum thickness (28). The wall (27) has an inner diameter (33) and an outer diameter (36). The top portion of the wall (27) has an inner diameter (39) and an outer diameter (38). The inner diameter tangent is a distance (37) from the center point of the short axis of the device and a distance (34) from the center point of the long axis of the device. The outer diameter tangent is a distance (35) from the center point of the short axis of the device and a distance (34) from the center point of the long axis of the device. The wall (27) does not completely encircle the first area, resulting in an opening (30). Angles (40) and (41) define the angle of the opening (30) as formed by the ends of the wall (27). Panel b) depicts a perspective view of one embodiment of the device of the present invention, showing an upper level or portion consisting of a wall (27) that partially encircles an area (10) of the lower level or portion that has a central or interior orifice (25), that has a smaller area than area (10). The central orifice (25) is set back a distance (23) from the wall (27). The wall (27) partially encircles the area (10), leaving an opening (30). The wall (27) has a base, and extends upward from the junction of the base and the area (10) of the lower level or portion. The lower portion also has two flanges (22a and 22b) that extend laterally outward from the first area (10) at the junction of the base of the wall (27).

For clarity of disclosure, and not by way of limitation, the detailed description of the invention is divided into the following subsections that describe or illustrate certain features, embodiments or applications of the present invention.

In one embodiment, the present invention provides a device that protects the skin surrounding an infant's navel from cleaning solutions, aids in manipulating the infant's umbilical cord stump, and provides support and protection to the infant's umbilical cord stump while a user cleans the infant's navel and umbilical cord stump. In one embodiment, the device of the present invention is used after the umbilical cord has been cut. In one embodiment, the device of the present invention is used to clean an infant's umbilical cord stump while a clamp is attached to the umbilical cord stump.

In one embodiment, the device of the present invention consists of an upper level or portion consisting of a wall (27) that partially encircles an area (10) of a lower level or portion that has a central or interior orifice (25), which is set back a distance (23) from the inner surface of the wall (27), and the area of the central orifice (25) is less than area (10). The wall (27) partially encircles the area (10), leaving an opening (30). The wall (27) has a base, and extends upward from the junction of the base and the area (10) of the lower level or portion, to a height (24). The lower portion also has two flanges (22a and 22b) that extend laterally outward from the first area (10) at the junction of the base of the wall (27). Each flange has fourth area. The lower portion has a height (26), and the device has a total height (32b).

In one embodiment, the device of the present invention comprises:
a. an upper portion and a lower portion, the upper portion consisting of a wall extending upward from a junction of the lower portion and a base of the wall, the upper portion defining by partially encircling a first area of the lower portion, the first area having a central orifice with a second area less than the first area, wherein the partial encirclement of the first area by the wall provides an opening; and b. a third area of the lower portion, consisting of two flanges extending laterally outward from the first area at the junction of the base of the wall of the upper portion and the first area of the lower portion, each flange having a fourth area.

The Upper Portion

In one embodiment, the upper portion of the device of the present invention is a wall (27) that extends upward from the lower portion, to a height (24). In one embodiment, the wall (27) is used to maneuver the device of the present invention. The user grips the device of the present invention by the wall (27) and may then place the device over the infant's umbilical cord stump, and maneuver the device once the device is placed over the umbilical cord stump.

In one embodiment, during cleaning, the user provides gentle downward pressure using the wall (27), such that the device provides a tight seal against the infant's skin, reducing the possibility of any chemical touching the infant's skin in areas that are not being cleaned.

In one embodiment, the wall (27) provides support to the umbilical cord stump while the infant's navel and umbilical cord stump are being cleaned. In a further embodiment, the wall (27) protects the umbilical cord stump while the infant's navel and umbilical cord stump are being cleaned.

The wall (27) may be any size and shape that is capable of providing protection to the umbilical cord stump. Referring to FIG. 1, panel b, in one embodiment, the wall (27) partially encircles an area (10) of a lower level or portion that has a central or interior orifice (25). The wall (27) partially encircles the area (10), leaving an opening (30). The wall (27) has a base, and extends upward from the junction of the base and the area (10) of the lower level or portion.

The perimeter of the central orifice (25) may be set back a distance (23) from the inner surface of the wall (27). In this instance, the area of the central orifice (25) is less than the first area (10). In an alternate embodiment, the perimeter of the central orifice is not set back a distance (23) from the inner surface of the wall (27). In this instance, the area of the central orifice (25) is the same as the first area (10).

The height (24) of the wall may be any height, provided the user can still access the infant's navel to clean the umbilical cord stump, while still providing adequate protection and support to the umbilical cord stump. In one embodiment, the height (24) may be greater than one inch. In one embodiment, the height (24) may be approximately 1 inch. In one embodiment, the height (24) is one inch. In an alternate embodiment, the height (24) is 0.9 inch. In an alternate embodiment, the height (24) is 0.8 inch. In an alternate embodiment, the height (24) is 0.7 inch. In an alternate embodiment, the height (24) is 0.6 inch. In an alternate embodiment, the height (24) is 0.5 inch. In an alternate embodiment, height (24) is 0.4 inch. In an alternate embodiment, the height (24) is 0.3 inch. In an alternate embodiment, the height (24) is 0.2 inch. In an alternate embodiment, the height (24) is 0.1 inch. In one embodiment, the height (24) is 0.421 inch.

The total height of the device (32*b*) may be any height, provided the user can still access the infant's navel to clean the umbilical cord stump, while still providing adequate protection and support to the umbilical cord stump and adequate protection to the infant's skin surrounding the navel. In one embodiment, the total height of the device (32*b*) is greater than one inch. In one embodiment, the total height of the device (32*b*) is approximately one inch. In one embodiment, the total height of the device (32*b*) is one inch. In an alternate embodiment, the total height of the device (32*b*) is 0.9 inch. In an alternate embodiment, the total height of the device (32*b*) is 0.8 inch. In an alternate embodiment, the total height of the device (32*b*) is 0.7 inch. In an alternate embodiment, the total height of the device (32*b*) is 0.6 inch. In an alternate embodiment, the height (24) is 0.5 inch. In one embodiment, the total height of the device (32*b*) is 0.616 inch.

The shape of the wall may be any shape, provided the user can still access the infant's navel to clean the umbilical cord stump, while still providing adequate protection and support to the umbilical cord stump. In one embodiment, the wall encircles an area (10). The wall may fully encircle the area (10). Alternatively, the wall may only partially encircle the area (10), leaving at least one opening (30). The at least one opening (30) may be any width that is capable of providing the user access to the infant's navel and umbilical cord stump to allow cleaning.

In one embodiment, the outer diameter (36) of the wall (27) is the same as the outer diameter (43) of the first area (10). In one embodiment, the outer diameter (36) is 1.590 inches.

In one embodiment, the inner diameter (33) of the wall (27) is less than the outer diameter (36) of the wall (27). In one embodiment, the inner diameter (33) is 1.450 inches. In certain embodiments, the center point of the inner diameter (33) and the center point of the outer diameter do not coincide. In these embodiments the wall (27) varies in thickness. An example of an embodiment of the device of the present invention where the center point of the inner diameter (33) and the center point of the outer diameter do not coincide is shown in FIG. 1, panel a).

The thickness of the wall (27) may be any value, provided the user can still access the infant's navel to clean the umbilical cord stump, while still providing adequate protection and support to the umbilical cord stump. The wall may be a uniform thickness. Alternatively, the wall may vary in thickness, having a minimum thickness (29) and a maximum thickness (28).

In the case where the wall (27) is a uniform thickness, the thickness may be any value. In one embodiment, the thickness can be any thickness from about 0.120 inches to about 0.265 inches.

In the case where the wall (27) varies in thickness, the minimum thickness (29) may be about 0.120 inches and the maximum thickness (28) may be about 0.265 inches.

The minimum thickness (29) can be located on either side of the at least one opening (30). Similarly, the maximum thickness (28) can be located on either side of the at least one opening (30).

In one embodiment, the at least one opening (30) provides access to the navel and umbilical cord stump to aid in cleaning the navel and umbilical cord stump. The width of the at least one opening (30) may be any width capable of providing access to the infant's navel and umbilical cord stump. In one embodiment, the opening (30) may be greater than one inch wide. In one embodiment, the at least one opening (30) may be approximately 1 inch wide. In one embodiment, the at least one opening is one inch wide. In an alternate embodiment, the at least one opening (30) is 0.9 inch wide. In an alternate embodiment, the at least one opening (30) is 0.8 inch wide. In an alternate embodiment, the at least one opening (30) is 0.7 inch wide. In an alternate embodiment, the at least one opening (30) is 0.6 inch wide. In an alternate embodiment, the at least one opening (30) is 0.5 inch wide. In an alternate embodiment, the at least one opening (30) is 0.4 inch wide. In an alternate embodiment, the at least one opening (30) is 0.3 inch wide. In an alternate embodiment, the at least one opening (30) is 0.2 inch wide. In an alternate embodiment, the at least one opening (30) is 0.1 inch wide.

In one embodiment, the device of the present invention has a single opening (30). The opening (30) may be located anywhere in the wall (27). In one embodiment, the opening (30) is located over the flange (22a). In an alternate embodiment, the opening is located over the flange (22b).

In an alternate embodiment, the device of the present invention has a first opening located over flange (22a) and a second opening located over flange (22b).

In an alternate embodiment, the at least one opening is located on the side of the wall (27) that is between the flanges.

In one embodiment, where the opening (30) is located over flange (22b), the minimum thickness (29) is located on the left side of the opening (30) and the maximum thickness (28) is located on the right side of the opening.

In one embodiment, where the opening (30) is located over flange (22b), the wall (27) is about 0.120 inches wide on the left side of the opening (30) and about 0.265 inches wide on the right side of the opening.

The Lower Portion

Figure 4:
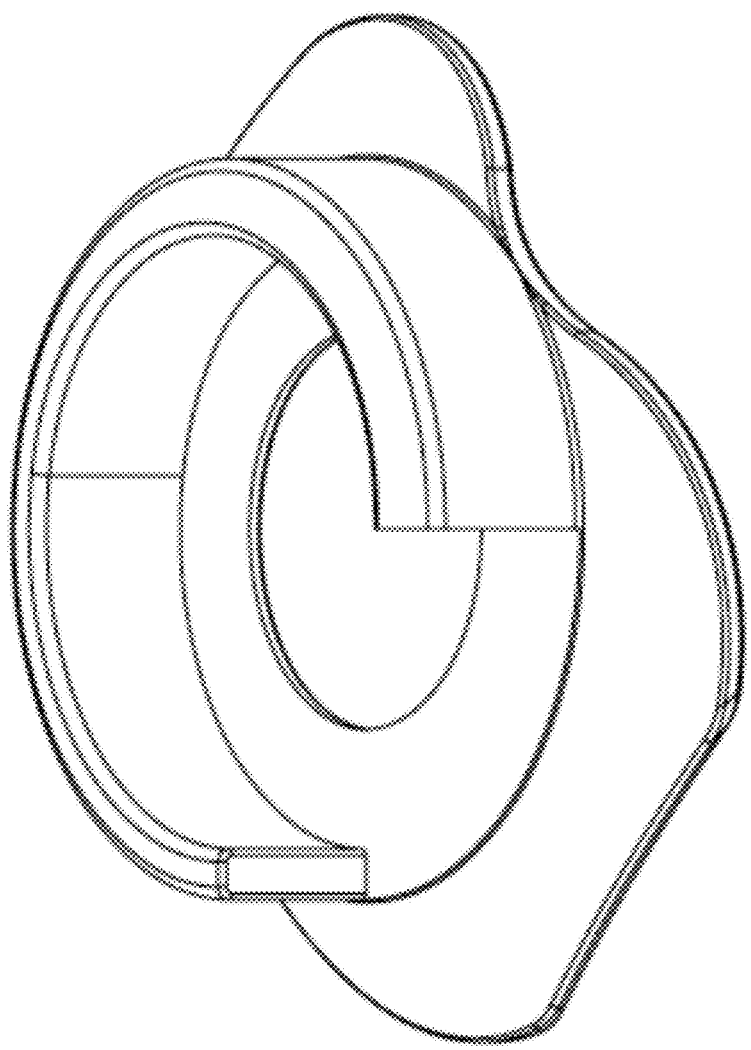
FIG. 4 depicts a perspective view of an alternate embodiment of the device of the present invention.

In one embodiment, the lower portion of the device of the present invention comprises a first area (10), a central orifice (25), the perimeter of which is a distance (23) from the inner surface of the wall (27) and two flanges (22a and 22b) that extend laterally outward from the first area (10) at the junction of the base of the wall of the upper portion (27). Using either FIG. 1 or 4 as guidance, it can be appreciated that the distance (23) varies according to the diameter of the central orifice (25) and the thickness of the wall.

In one embodiment, the lower portion protects the skin surrounding the infant's navel from cleaning solutions while the infant's navel and umbilical cord stump are being cleaned.

In one embodiment, the lower portion manipulates the infant's umbilical cord stump. The device of the present invention is placed over the infant's umbilical cord stump, such that the umbilical cord stump passes through the central orifice (25). In one embodiment, when the device of the present invention is moved, the perimeter of the central orifice (25) contacts the umbilical cord stump, displacing the umbilical cord stump slightly, exposing the area between the stump and the navel, allowing the exposed area to be cleaned.

The first area (10) may be any size and shape that is capable of protecting the skin surrounding the infants navel and still capable of allowing the user access to clean the umbilical cord stump. In one embodiment, the first area (10) is circular and has a diameter (43) equivalent to the outer diameter (36) of the wall (27) of the upper portion. In one embodiment, the first area (10) is circular and has a diameter (43) of 1.590 inches.

The perimeter of the central orifice (25) may be set back a distance (23) from the inner surface of the wall (27). In this instance, the area of the central orifice (25) is less than the first area (10). In an alternate embodiment, the perimeter of the central orifice (25) is not set back a distance (23) from the inner surface of the wall (27). In this instance, the area of the central orifice (25) is the same as the first area (10).

In embodiments where the perimeter of the central orifice (25) is not set back a distance (23) from the inner surface of the wall (27), the perimeter of the central orifice and the inner surface of the wall (27) may contact the umbilical cord stump.

In embodiments where the perimeter of the central orifice (25) is set back a distance (23) from the inner surface of the wall (27), the perimeter of the central orifice (25) alone may contact the umbilical cord stump.

In embodiments where the perimeter of the central orifice (25) is set back a distance (23) from the inner surface of the wall (27), the device of the present invention may further comprise an optional absorbent pad, or similar material, that is placed in the area (10). The absorbent pad, or similar material may absorb any fluids, such as cleaning materials that may be spilled during cleaning the infant's umbilical cord stump and navel.

Figure 5:
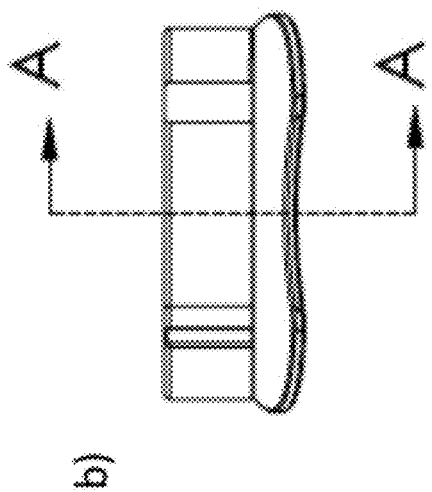
FIG. 5, panel a) is a cross-sectional view of one embodiment of the device of the present invention, sectioned according to the line A-A as shown in panel b). The height of the perimeter of the central orifice is shown in (31).
Figure 5:
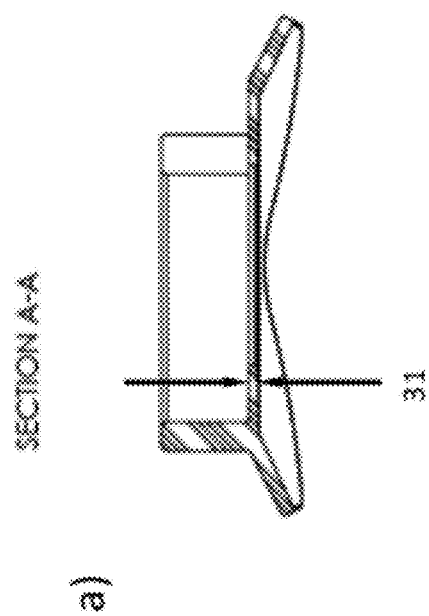

Referring to FIG. 5 for guidance, the perimeter of the central orifice (25) has a height (31). The height (31) may be any value suitable to manipulate the umbilical cord stump with the device of the present invention without damaging or severing the umbilical cord stump. In one embodiment, the height (31) is the difference between the total height of the device (32b) less the height as measured from the upper surface of the tip of the flanges (32a). In one embodiment, the height (31) is 0.048 inches.

The size of the central orifice (25) may be any size capable of accepting an umbilical cord stump with or without a clamp attached and providing sufficient space to manipulate the device of the present invention and allow access for the user to clean the umbilical cord stump and navel.

Similarly, the shape of the central orifice (25) may be any shape capable of accepting an umbilical cord stump with or without a clamp attached and providing sufficient space to manipulate the device of the present invention and allow access for the user to clean the umbilical cord stump and navel. In one embodiment, the central orifice (25) is circular. In one embodiment, the central orifice (25) is of a size capable of accepting umbilical cord stumps up to one inch in diameter, and still providing sufficient space to manipulate the device of the present invention and allow access for the user to clean the umbilical cord stump and navel. In one embodiment, the central orifice (25) has a diameter (42) of ⅞ inch. In an alternate embodiment, the central orifice has a diameter (42) of one inch. In an alternate embodiment, the central orifice has a diameter (42) of one and 3/16 inch.

In one embodiment, the lower portion has third area, comprising two flanges extending laterally outward from the first area at the junction of the base of the wall of the upper portion and the first area of the lower portion, each flange having a fourth area. The area of each flange may be equal. Alternatively, one flange may be larger than the other.

The total area of the lower portion may be any value that is capable of protecting the skin surrounding the infant's navel from cleaning solutions while the infant's navel and umbilical cord stump are being cleaned. The total area of the lower portion is the sum of the first area, the second area, and the third area (which itself is the sum of the two fourth areas).

Figure 2:
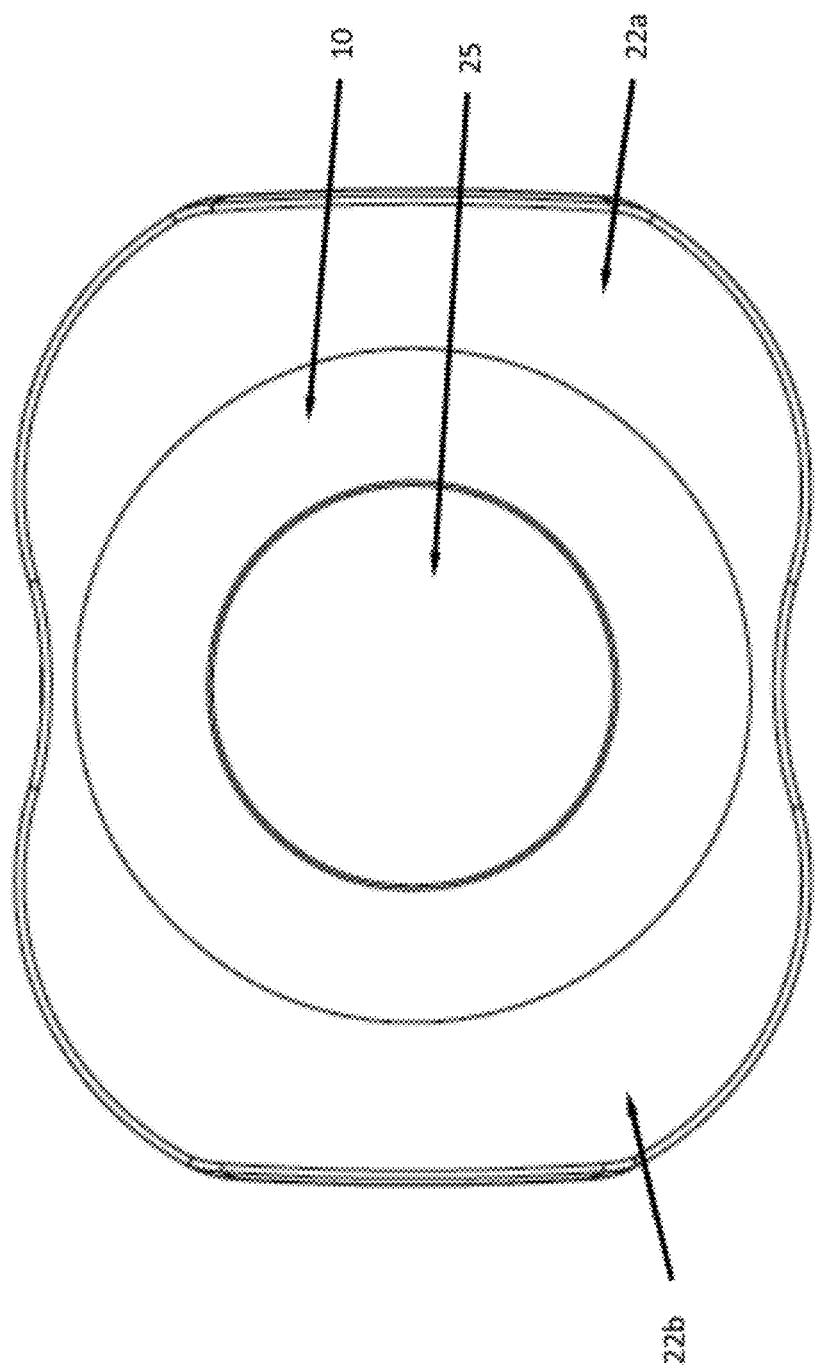
FIG. 2 depicts a plan view of one embodiment of the device of the present invention, looking from the bottom, showing the bottom surface of the lower portion of the device of the present invention, comprising the underside of the area (10) of the lower level or portion that has a central or interior orifice (25), that has a smaller area than area (10). The two flanges (22a and 22b) that extend laterally outward from the first area (10) area are also shown.

The flanges (22a & 22b) may be any shape. In one embodiment, the flanges (22a & 22b) are the shape shown in FIG. 2.

Figure 3:
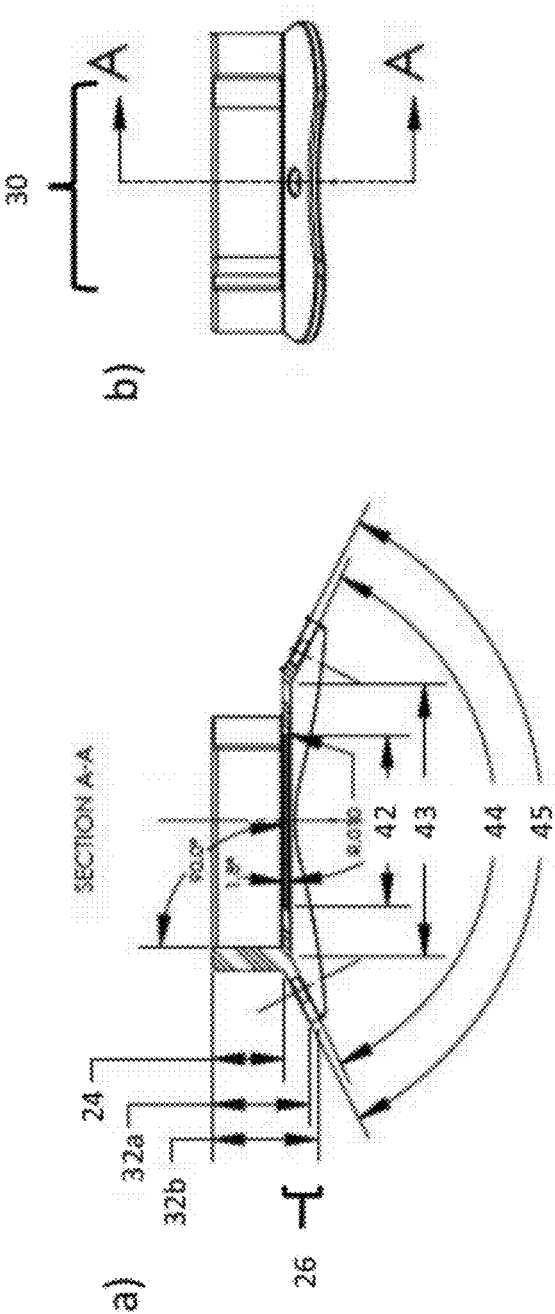
FIG. 3 panel a) depicts a cross-sectional view of one embodiment of the device of the present invention, sectioned according to the line A-A as shown in panel b). The upper portion has a height (24). The lower portion has a height (26), which corresponds in part to the downward deflection of the flanges (22 a & b). The device has a total height (32b) and a height as measured from the upper surface of the tip of the flanges (32a). The central orifice has a diameter (42), and the first area (10) has a diameter (43). The angles of deflection of the lower surface of the flanges (45) and the upper surface of the flanges (45) are also shown. Panel b) depicts a side view of one embodiment of the device of the present invention showing an upper level or portion consisting of a wall that partially encircles an area of the lower level or portion and the opening (30). The wall has a base, and extends upward from the junction of the base and the area of the lower level or portion. The lower portion also has two flanges that extend laterally outward from the first area at the junction of the base of the wall.

In one embodiment, the flanges (22a & 22b) extend laterally outward from the first area (10) at the junction of the base of the wall (27) of the upper portion and the first area (10) of the lower portion. Referring to FIG. 3, in one embodiment, the flanges (22a & 22b) extend laterally outward and downward, forming a lower portion, having a height (26) that conforms to the shape of the infant's abdomen. The angle of the downward deflection of the flanges (22a & 22b) may be any angle that is capable of conforming to the shape of the infant's abdomen. In one embodiment, the angle of downward deflection (45) of the upper surface of the flanges is 126 degrees. In one embodiment, the angle of downward deflection (44) of the lower surface of the flanges is 130 degrees.

In one embodiment, the lower portion of the device of the present invention is approximately 1.875 inches wide and 2.350 inches in length. However, the lower portion of the device of the present invention can be any size.

Use of the Device of the Present Invention

The device of the present invention may be used by a left-handed, or a right-handed user.

The device of the present invention may be used once, and then disposed. Alternatively, the device of the present invention may be reused. The device of the present invention may be provided within a package that may, or may not be sterile. The package may also contain solutions that may be used to clean the infant's umbilical cord. Such solutions may include, for example, hydrogen peroxide solution, isopropyl alcohol, anti microbial solutions, anti bacterial solutions and the like. The package may also include items, such as, for example, cotton swabs, cotton wool, towelettes, sterile wipes and the like.

In one embodiment, the package may also include instructions on how to use the device of the present invention.

The device of the present invention is suitable for use in a hospital or other medical facility, or a home environment.

To clean an infant's navel and umbilical cord stump, in one embodiment, the user of the device of the present invention places the infant on its back and places the device of the present invention over the infant's navel, such that the umbilical cord stump passes through the central orifice (25). The device is oriented such that the upper portion faces away from the infant, and the lower portion touches the infant's abdomen.

In one embodiment, the user manipulates the umbilical cord stump, exposing areas of the stump to be cleaned by moving the device of the present invention, causing the umbilical cord stump to touch the perimeter of the central orifice (25). The touching of the umbilical cord stump to the perimeter of the central orifice (25), together with movement of the device of the present invention, displaces the umbilical cord stump. In this embodiment, the user does not touch the umbilical cord stump directly.

In one embodiment, displacement of the umbilical cord stump exposes areas of the umbilical cord stump that were previously inaccessible. The user may then clean the exposed areas. In one embodiment, the user may simply wipe the exposed areas. In an alternate embodiment, the user may employ a cleaning solution to clean the exposed areas. In one embodiment, the device of the present invention protects the skin surrounding the area being cleaned from the cleaning solutions being used. In one embodiment, the device of the present invention may further comprise an optional absorbent pad, or similar material, that is placed in the area (10). The absorbent pad, or similar material may absorb any fluids, such as cleaning materials that may be spilled during cleaning the infant's umbilical cord stump and navel.

In an alternate embodiment, the user of the device of the present invention places the infant on its back and places the device of the present invention over the infant's navel, such that the umbilical cord stump passes through the central orifice (25). The device is oriented such that the upper portion faces away from the infant, and the lower portion touches the infant's abdomen. The user then cleans the infant's umbilical cord stump.

In one embodiment, the user utilizes gentle downward pressure to ensure the device of the present invention maintains a close contact with the infant's abdomen. In an alternate embodiment, the user may employ a cleaning solution to clean the umbilical cord stump. In one embodiment, the device of the present invention protects the skin surrounding the area being cleaned from the cleaning solutions being used. In one embodiment, the device of the present invention may further comprise an optional absorbent pad, or similar material, that is placed in the area (10). The absorbent pad, or similar material may absorb any fluids, such as cleaning materials that may be spilled during cleaning the infant's umbilical cord stump and navel. The user may then move the device of the present invention, exposing areas of the umbilical cord stump that were previously inaccessible. The user may then clean the exposed areas.

Manufacturing the Device of the Present Invention

The device of the present invention may be molded as a single piece of material. Alternatively, the device of the present invention may be machined or manufactured according to other methods known in the art. The device of the present invention may be manufactured from any material that is capable of providing support to the umbilical cord that can aid in manipulating the umbilical cord and can protect the infant's skin from the chemicals used to claim the umbilical cord. In one embodiment, the device of the present invention is manufactured from non-absorb ent plastic. In one embodiment, the upper portion and the lower portion may be manufactured separately and attached through methods known in the art. In one embodiment, different size upper portions may be interchangeable with different size lower portions.

Although a variety of plastics may be used to manufacture the device of the present invention, in one embodiment, the device of the present invention is manufactured from a plastic that is phthalates free. In one embodiment, the device of the present invention is manufactured from polypropylene.

The device of the present invention may be manufactured in any color, such as, for example, blue, green, purple, pink, white, and the like. The device of the present invention may be manufactured in one, or more than one color.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A device that protects the skin surrounding an infant's navel from cleaning solutions, aids in manipulating the infant's umbilical cord stump, and provides support and protection to the infant's umbilical cord stump while a user cleans the infant's navel and umbilical cord stump, consisting of:

a. a non-absorbent upper portion and a non-absorbent lower portion, the non-absorbent upper portion consisting of a wall extending upward from a junction of the non-absorbent lower portion and a base of the wall, the non-absorbent upper portion defining, by partially encircling a first area of the non-absorbent lower portion, the first area having a continuous surface and a central orifice that is completely encircled by the first area of the non-absorbent lower portion, having a second area less than the first area, wherein the partial encirclement of the first area by the wall defines an opening; and b. a third area of the non-absorbent lower portion, consisting of two flanges extending laterally outward from the first area at the junction of the base of the wall of the non-absorbent upper portion and the first area of the non-absorbent lower portion, each flange having a fourth area.

2. The device of claim 1, wherein the wall of the non-absorbent upper portion has a variable thickness.

3. The device of claim 1, wherein the central orifice can accept an umbilical cord stump of up to 1 inch in diameter.

4. The device of claim 1, wherein the central orifice can accept an umbilical cord stump that has a clamp attached.

5. The device of claim 1, wherein the central orifice is circular.

6. The device of claim 1, wherein the non-absorbent lower portion is capable of protecting the skin surrounding an infant's navel from cleaning solutions while the infant's navel and umbilical cord stump are being cleaned.

7. The device of claim 1, wherein the non-absorbent upper portion is capable of protecting the infant's umbilical cord stump.

8. The device of claim 1, wherein the non-absorbent lower portion is capable of manipulating the infant's umbilical cord stump.

9. The device of claim 1, wherein the non-absorbent upper portion is capable of supporting the infant's umbilical cord stump.

10. The device of claim 1, wherein the user does not physically hold the infant's umbilical cord stump.

11. The device of claim 1, wherein the user utilizes the device of the present invention to manipulate the infant's umbilical cord stump to expose areas to be cleaned.

12. The device of claim 1, wherein said device is a single unit manufactured by an injection molding process.

13. The device of claim 1, wherein the device is manufactured from a material that is phthalates free.

14. The device of claim 1, wherein said device is made from polypropylene.

\* \* \* \* \*